(12) United States Patent
Knudsen

(10) Patent No.: US 7,947,471 B2
(45) Date of Patent: May 24, 2011

(54) METHOD OF PRODUCTION OF RECOMBINANT PROTEINS IN EUKARYOTE CELLS

(75) Inventor: Ida Mølgaard Knudsen, Værløse (DK)

(73) Assignee: Novo Nordisk Health Care A/G, Zurich (CH)

( * ) Notice: Subject to any disclaimer, the term of this patent is extended or adjusted under 35 U.S.C. 154(b) by 542 days.

(21) Appl. No.: 11/851,549

(22) Filed: Sep. 7, 2007

(65) Prior Publication Data

US 2008/0064068 A1 Mar. 13, 2008

Related U.S. Application Data

(63) Continuation of application No. 11/429,558, filed on May 5, 2006, now abandoned.

(51) Int. Cl.
*C12P 21/06* (2006.01)
*C12N 5/00* (2006.01)
(52) U.S. Cl. ........................ 435/69.1; 435/325
(58) Field of Classification Search .................. None
See application file for complete search history.

(56) References Cited

U.S. PATENT DOCUMENTS

| | | | |
|---|---|---|---|
| 4,189,534 A | 2/1980 | Levine et al. | |
| 4,335,215 A * | 6/1982 | Tolbert et al. | ............... 435/403 |
| 4,357,422 A | 11/1982 | Giard et al. | |
| 4,664,912 A | 5/1987 | Wiktor et al. | |
| 4,783,940 A | 11/1988 | Sato et al. | |
| 4,978,616 A | 12/1990 | Dean, Jr. et al. | |
| 5,015,576 A | 5/1991 | Nilsson et al. | |
| 5,510,328 A | 4/1996 | Polarek et al. | |
| 5,576,194 A | 11/1996 | Chan | |
| 5,580,560 A | 12/1996 | Nicolaisen et al. | |
| 5,654,197 A | 8/1997 | Jem et al. | |
| 5,661,008 A | 8/1997 | Almstedt et al. | |
| 6,100,061 A * | 8/2000 | Reiter et al. | ............... 435/69.1 |
| 6,358,534 B1 * | 3/2002 | Schwarz et al. | ............... 424/529 |
| 6,458,565 B1 | 10/2002 | Cunningham et al. | |
| 6,475,725 B1 | 11/2002 | Reiter et al. | |
| 6,936,441 B2 | 8/2005 | Reiter et al. | |

FOREIGN PATENT DOCUMENTS

| | | |
|---|---|---|
| EP | 0 212 880 | 3/1987 |
| JP | 57-71391 | 5/1982 |
| JP | 57-501265 | 7/1982 |
| JP | 2001-524953 | 12/2001 |
| WO | WO 9322425 | 11/1993 |
| WO | WO 9322448 | 11/1993 |
| WO | WO 95/13361 | 5/1995 |

(Continued)

OTHER PUBLICATIONS

Wang et al., Bead to bead transfer of Vero cells in microcarrier culture., Bioprocess Engineering, 1999, vol. 21, pp. 211-213.*

(Continued)

*Primary Examiner* — Alexander D Kim
(74) *Attorney, Agent, or Firm* — Rosemarie R. Wilk-Oresean

(57) ABSTRACT

The invention provides a method for production of polypeptides in eukaryote microcarrier cell culture, the method comprising the steps of (i) Culturing cells expressing said polypeptide on microcarriers under conditions and at a setpoint temperature appropriate for expression of said polypeptide; (ii) Cooling the culture to a predetermined temperature below said setpoint; (iii) Sedimenting the microcarriers; and (iv) Harvesting all or part of the culture medium.

10 Claims, 2 Drawing Sheets

FOREIGN PATENT DOCUMENTS

Figure 1:
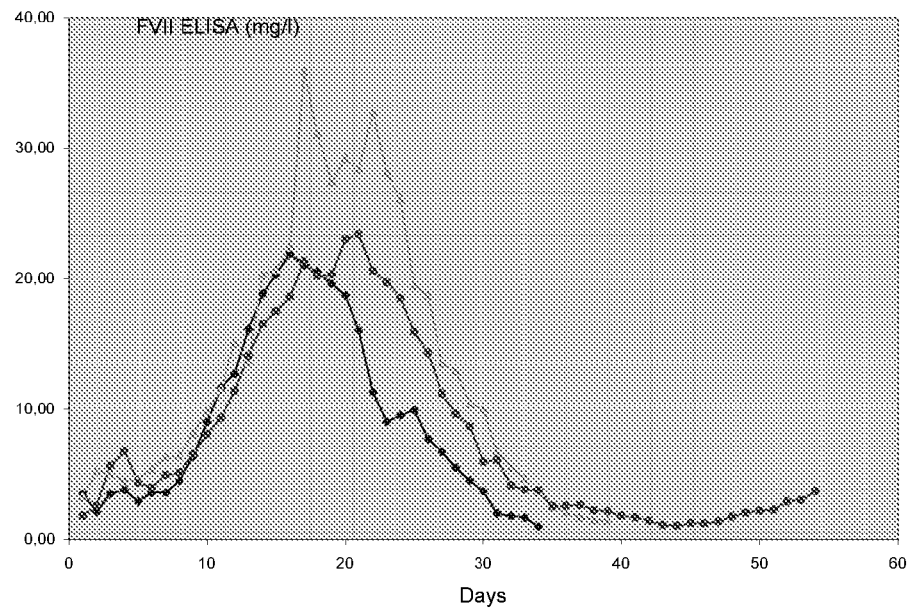

| | | |
|---|---|---|
| WO | WO 9804680 | 2/1998 |
| WO | WO 0028065 | 5/2000 |
| WO | WO 0111021 | 2/2001 |
| WO | WO 02/29083 | 4/2002 |
| WO | WO 02/29084 | 4/2002 |

OTHER PUBLICATIONS

Bankamp et al., adaptation to cell culture induces functional differences in measles virus proteins., Virology Journal, 2008, vol. 5, pp. 1-12.*
Shou et al., Large-scale mammalian cell culture., Current Opinion in biotechnology, 1997, vol. 8, pp. 148-153.*
Wagner et al., Biotechnology and Bioengineering, vol. 36, No. 6, pp. 623-629 (1990).
Kennard et al., Biotechnology and Bioengineering, vol. 47, No. 5, pp. 550-556 (1995).
Sunderji et al., Biotechnology and Bioengineering, vol. 55, No. 1, pp. 136-147 (1997).
Wen et al., J. Biotechnol., vol. 79, pp. 11 (2000).
Jurlander et al., Sem. Thromb. Hemost., vol. 27 (4), pp. 373-383 (Aug. 2001).
Persson et al., Biochemistry, vol. 40, pp. 3251-3256 (Mar. 2001).
Persson et al., J. Biol Chem., vol. 276 (31), pp. 29195-29199 (Aug. 2001).
Broad et al., Cytotechnology, vol. 5(1), pp. 47-55 (1991).
Goudemand, Transfusion Clinique et Biologique, vol. 5(4), pp. 260-265 (1998).
Kemball-Clark et al., Gene, vol. 139 (2), pp. 275-279 (1994).
Roddie et al., Blood Reviews, vol. 11 (4), pp. 169-177 (1997).
Sinacore et al., Biotech and Bioeng, vol. 52, pp. 518-528 (1996).
Zang et al., Bio/Tech, vol. 13, pp. 389-392 (1995).
Xie et al., Trends in Biotech, vol. 15(3), pp. 109-113 (1997).
Bragonzi et al., Biochimica et Biophysica Acta, vol. 1474, pp. 273-282 (2000.
Bjoern et al., J of Biol Cehm, vol. 266(17), pp. 11051-11057 (1991).
Gawlitzek et al., J of Biotech, vol. 42, pp. 117-131 (1995).
Grabenhorst et al., Glycoconjugate J, vol. 16, pp. 81-97 (1999).
Klausen et al., Molec Biotech, vol. 9, pp. 195-204 (1998).
Klausen et al., J of Chromatog A, vol. 718, pp. 195-202 (1995).
Thim et al., Biochem, vol. 27(20), pp. 7785-7793 (1988).
Chen et al., Curr Proto in Protein Sci, vol. 5.10, pp. 1-2, pp. 14-22 (1998).
Reiter et al., Cytotech, vol. 3(3), pp. 271-277 (1990).
Gayle et al., J Biol Chem, vol. 268(29), pp. 22105-22111 (Oct. 1993).
Whisstock et al., Q Rev Biophys, vol. 36 (3), pp. 307-340 (2003).
Ragni et al., Haemophilia, vol. 7 (Suppl 1), pp. 28-35 (Jan. 2001).
Schmidtchen et al., Am J Hum Genet., vol. 62 (1), pp. 64-69 (Jan. 1998).
Weber et al., Analytical Biotechnology, vol. 225, pp. 135-142 (1995).
Weikert et al., Nature Biotech, vol. 17, pp. 1116-1121 (1994).
Jenkins et al., Enzyme Microb Tech, vol. 16, pp. 354-364 (1994).
Nakagaki et al., Biochem, vol. 30 (45), pp. 10819-10824 (1991).
Wickham & Nemerow (1993) Biotechnol. Prog. vol. 9, pp. 25-30.

* cited by examiner

SEQUENCE LISTING

```
<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
agcgttttag cgccggcgcc ggtgcaggac                                    30

<210> SEQ ID NO 2
<211> LENGTH: 38
<212> TYPE: DNA
<213> ORGANISM: Artificial Sequence
<220> FEATURE:
<223> OTHER INFORMATION: Primer

<400> SEQUENCE: 2
cgccggcgct aaaacgcttt cctggaggag ctgcggcc                           38
```

METHOD OF PRODUCTION OF RECOMBINANT PROTEINS IN EUKARYOTE CELLS

CROSS-REFERENCE TO RELATED APPLICATIONS

This application is a continuation of U.S. application Ser. No. 11/429,558 filed May 5, 2006 which is a continuation of U.S. application Ser. No. 10/254,394 and claims priority of PCT application no. PCT/DK01/00632 filed Oct. 2, 2001, PCT application no. PCT/DK01/00634 filed Oct. 2, 2001, Danish application no. PA 2002 00460 filed Mar. 26, 2002 and U.S. application No. 60/374,855 filed Apr. 10, 2002, the contents of which are fully incorporated herein by reference.

FIELD OF THE INVENTION

The present invention relates to methods for cultivating eukaryote cells and for producing recombinant proteins in large-scale or industrial scale cultures of such cells.

BACKGROUND OF THE INVENTION

Microcarrier culture is widely used within the cell culture area. In microcarrier culture the cells are either immobilised by attachment onto the surface of solid microcarriers or by attachment to or physical entrapment inside the internal structure of macroporous microcarriers. When using microcarrier culture a methodology is needed for retaining the carriers with cells in the culture vessel whilst harvesting the culture supernatant. One microcarrier-based process type is the continuous perfusion process, where culture supernatant is continuously harvested and new medium continuously added. In this process type the microcarriers are typically retained by means of a gravitational settler or an internal filter in the culture vessel. Another microcarrier-based process type is the semi-continuous process where batch wise harvesting of culture supernatant and addition of new medium is performed with regular intervals. In this process type the microcarriers are most easily retained by stopping the agitator of the culture vessel and thereby letting the carriers with cells sediment at the bottom of the vessel. When the cell-containing carriers have sedimented part of the culture supernatant is harvested and replaced with new medium, where after the agitator is started again. However, the lack of agitation during sedimentation endangers the cells of being subjected to lack of oxygen or nutrients. The present invention provides an improved method which improves the ability of the cells to withstand the conditions while they are sedimented at the bottom of the vessel and thus have a positive effect on the overall performance of the culture.

SUMMARY OF THE INVENTION

The present invention provides an improved method for culturing cells, in particular producing desired polypeptides, characterised in that it includes a cooling step prior to the sedimentation of carriers and harvest of product-containing culture supernatant.

In one aspect, the invention provides a method for production of polypeptides in eukaryote cells, comprising the steps of (i) Culturing cells expressing said polypeptide on microcarriers under conditions and at a setpoint temperature appropriate for expression of said polypeptide; (ii) Cooling the culture to a predetermined temperature below said setpoint; (iii) Sedimenting the microcarriers; and (iv) Harvesting all or part of the culture medium.

In some embodiments the method further comprises a step of adding fresh medium to the culture vessel after said harvesting.

In some embodiments the method further comprises a step of recovering said polypeptide from the harvested culture medium.

In another aspect, the invention provides a method for cultivation of eukaryote cells, comprising the steps of (i) Culturing cells on microcarriers under conditions and at a setpoint temperature appropriate for maintaining the culture; (ii) Cooling the culture to a predetermined temperature below said setpoint; (iii) Sedimenting the microcarriers; and (iv) Harvesting all or part of the culture medium.

In some embodiments the methods further comprises a step of adding fresh medium to the culture vessel after said harvesting.

In some embodiments the method is a large-scale or industrial-scale method.

In another aspect the invention provides a method for harvesting polypeptides produced by eukaryotic cells growing in microcarrier culture, said method comprising (i) cooling the culture to a predetermined temperature below the setpoint of the cultivation, followed by (ii) sedimenting the microcarriers.

In some embodiments, prior to allowing the carriers to sediment, the culture is cooled from the growth temperature to a temperature between about 5° C. and 30° C. below the temperature setpoint of the cultivation, or between about 5° C. and 20° C. below the setpoint, or between 5° C. and 15° C. below the setpoint, or about 5° C., 10° C., 15° C. or 20° C. below the temperature setpoint of the cultivation.

In some embodiments the culture is cooled to a temperature between about 18° C. and about 32° C. before allowing the carriers to sediment, or between about 20° C. and about 30° C., or between about 22° C. and about 28° C., or between about 24° C. and about 28° C., or between about 25° C. and about 27° C.

In some embodiments, the cells used are insect cells. In some embodiments, the cells used are mammalian cells. In some embodiments thereof, the cells used are BHK cells; in other embodiments, the cells are CHO cells; in other embodiments, the cells are HEK cells; in other embodiments, the cells are COS cells; in other embodiments, the cells are HeLa cells. Preferred are BHK and CHO cells, in particular CHO cells.

In some embodiments the microcarriers are solid carriers; in some embodiments the microcarriers are macroporous carriers; in some embodiments the microcarriers are macroporous carriers having a positive surface charge.

In some embodiments, the cells produce a desired polypeptide, preferably a clotting factor and most preferably human factor VII or a human factor VII-related polypeptide, including, without limitation, wild-type Factor VII, L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, S336G-FVII; S52A-Factor VII, S60A-Factor VII; R152E-Factor VII, S344A-Factor VII, Factor VIIa lacking the Gla domain; and P11Q/K33E-FVII, T106N-FVII, K143N/N145T-FVII, V253N-FVII, R290N/A292T-FVII, G291N-FVII, R315N/V317T-FVII, K143N/N145T/R315N/ V317T-FVII; and FVII having substitutions, additions or deletions in the amino acid sequence from 233Thr to 240Asn, FVII having substitutions, additions or deletions in the amino acid sequence from 304Arg to 329Cys.

In some embodiments, the protein expressed is human factor VII. In other embodiments, the protein expressed is factor VII having substantially the same or improved biological activity compared to wild-type FVII. In other embodiments, the protein expressed is a factor VII-related polypeptide having modified or reduced biological activity compared to wild-type FVII. In other embodiments, the protein expressed is FVIII, FIX, FX, FII, protein C, a plasminogen activator (t-PA, u-PA), PDGF, VEGF, growth hormone, insulin, interleukin, interferon, or an antibody, or a fragment of said proteins.

In some embodiments the cultured eukaryote cells are recombinant cells, transformed or transfected with a vector prepared by in vitro gene recombination. In some embodiments the cells are human cells expressing an endogenous factor VII gene.

In some embodiments the desired polypeptide is produced at a level at least about 15 mg/l of culture.

In some embodiments, the cells used in practising the present invention are attachment dependent cells attached to the surface of solid carriers or inside the internal structure of macroporous carriers by cellular adhesion. In other embodiments, the cells used in practising the pre-sent invention are suspension cells captured inside the internal structure of macroporous carriers by physical entrapment.

In a particularly preferred embodiment, the host cells are BHK 21 or CHO cells that have been engineered to express human factor VII or human factor VII-related polypeptides and that have been adapted to grow in the absence of serum and other animal-derived components.

In one series of embodiments the medium is a medium lacking animal-derived components. In other embodiments the medium lacks animal-derived components and lacks proteins ("protein-free").

In one embodiment the cells are CHO cells, the polypeptide is human factor VII, the carriers are macroporous carriers, the medium is a protein free medium free of animal-derived components, the cells are CHO cells, the culture temperature setpoint is about 36° C., and the temperature to which the culture is cooled before sedimentation of carriers is about 26° C.

LIST OF FIGURES

FVII titres in the cultivations FFF 1235, FFF 1239, and FFF 1242 are shown graphically in FIG. 1 (overview of cultivations with CHO cells on Cytopore carriers in 500 L culture vessels).

Figure 2:
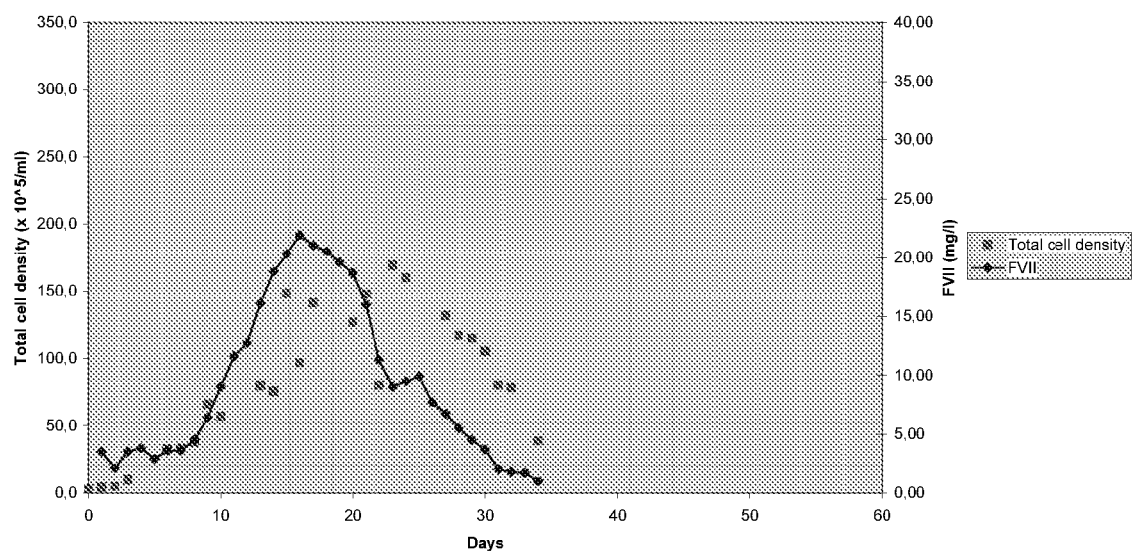
Figure 3:
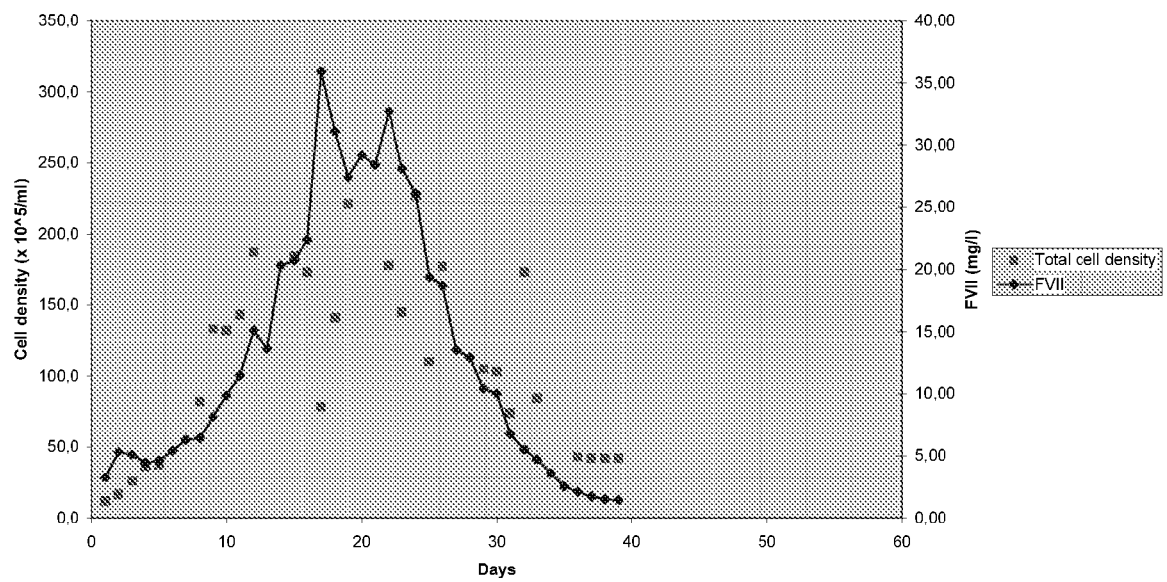
Figure 4:
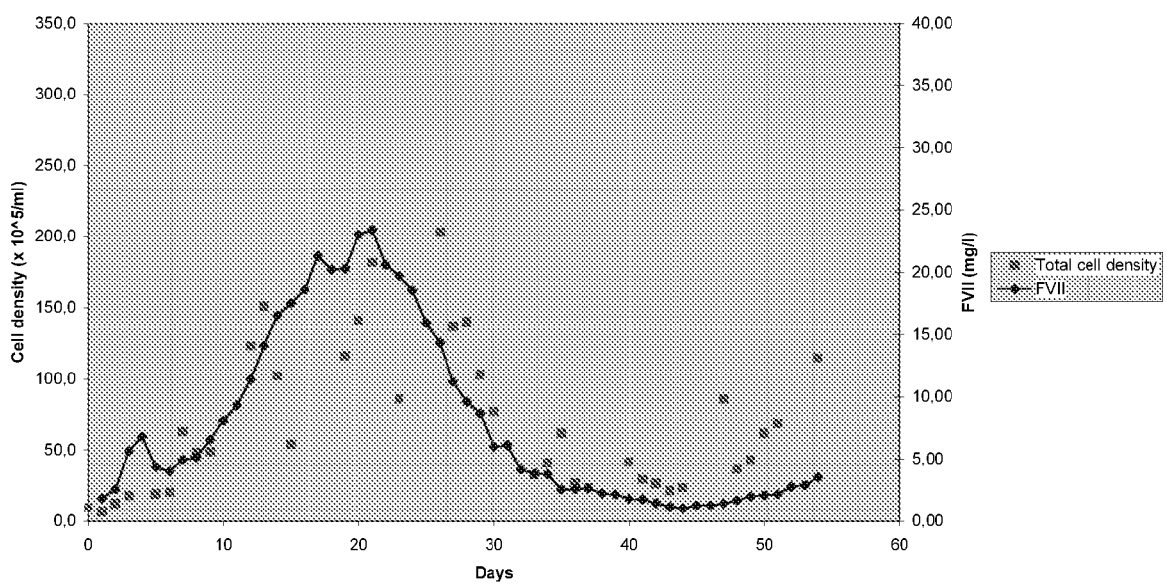

Cell counts and FVII titres for cultivations FFF 1235, FFF 1239, and FFF 1242 are shown in FIG. 2 to FIG. 4: FFF 1235, cell counts and FVII titres (FIG. 2); FFF 1239, cell counts and FVII titres (FIG. 3) and FFF 1242, cell counts and FVII titres (FIG. 4).

DETAILED DESCRIPTION OF THE INVENTION

The present invention provides methods for microcarrier based cultivation of eukaryote cells, particularly to produce large-scale or industrial amounts of desired polypeptides that are expressed by such cells. The cultivation process type in question is a microcarrier-based process type with batch-wise harvesting of culture supernatant after sedimentation of carriers.

It has been found that application of a cooling step before the sedimentation of the cell-containing carriers has a positive effect on the overall performance of the culture.

Without wishing to be bound by scientific theory it is believed that the cooling step increases the ability of the cells to withstand the conditions while they are sedimented at the bottom of the culture vessel. This, in turn, has a positive effect on the overall performance of the culture. During the sedimentation period, which lasts for about one hour in a 500 L culture vessel, no oxygen control can be performed, and the concentration of dissolved oxygen rapidly decreases.

When employing the herein described type of microcarrier process, the temperature control loop of the culture vessel is traditionally de-activated before sedimentation of carriers; however, no active cooling of the culture vessel is performed. The only purpose of de-activating the temperature control loop is to prevent local overheating of the cells while they are sedimented at the bottom of the culture vessel. The de-activation does not result in actual cooling of the culture vessel, and typically the temperature decrease is less than 1° C. It has been found that by employing a cooling step according to the present invention, a cooling of, e.g., 10° C. below the temperature setpoint of the cultivation, such as, e.g., to 26° C., the oxygen requirements of the cells (as measured by oxygen consumption) are reduced by about 50%. Cooling to 20° C. reduced the oxygen requirements of the cells by about 75%. The culture is cooled to a predetermined temperature below the temperature setpoint of the cultivation (e.g. between about 5° C. and 30° C., or between about 5° C. and 20° C., or between about 5° C. and 15° C., or to about 5° C., 10° C., 15° C. or 20° C. below the setpoint).

The cooling step according to the invention is applied immediately before the sedimentation of carriers. As used herein, "immediately before" means that as soon as the contents of the culture vessel has been cooled down to the pre-determined temperature, the cooling is stopped and the agitation of the vessel is stopped to allow the carriers with cells to sediment at the bottom of the vessel.

The duration of the cooling step typically requires from 10 to 240 minutes, such as, e.g, from 20 to 180 minutes, or from 30 to 120 minutes, depending on the size of the culture vessel, the desired temperature lowering and the cooling method employed; however, a cooling step of any duration is encompassed by the present invention. The cooling step is thus normally initiated from about 10 to about 240 minutes before allowing the cell-containing microcarriers to sediment. For example, lowering the temperature of a 500 l culture vessel from a culturing temperature of 36° C. to 26° C. by supplying cooling water to the jacket of the culture vessel typically takes about 30 minutes; lowering the temperature of a 5000 l culture vessel from a culturing temperature of 36° C. to 26° C. by supplying cooling water to the jacket of the culture vessel typically also takes about 30 minutes.

The step is typically carried out as follows: The temperature control loop of the culture vessel is deactivated and the culture vessel is cooled, for example by keeping the valve for cooling water to the jacket of the culture vessel constantly open. The temperature is continuously monitored and when the contents of the culture vessel reaches a pre-determined temperature below the setpoint temperature, such as, e.g., 10° C. below the set point of the culturing, the cooling is stopped. Thereafter, the agitator of the culture vessel is stopped whereby the cell-containing carriers are allowed to sediment.

After sedimentation part of the culture supernatant or medium is harvested and fresh medium is added to the culture vessel to replace the harvested medium. When the culture supernatant has been harvested and new medium has been added, the agitator is started and the temperature is again regulated to the setpoint for the cultivation by activating the temperature control loop. The fresh media being added is typically pre-heated to a temperature close to the setpoint of the cultivation, e.g., to about 30° C., or above, depending on the actual setpoint.

In practising the present invention, any effective method for cooling the culture may be employed. The culture vessel may, for example, be cooled by supplying cooling water to the jacket of the culture vessel for a sufficient period of time until the desired temperature is reached, or the culture vessel may be equipped with a cooling coil which may then be used alone or in combination with the above-mentioned cooling of the jacket.

Cell culture procedures: The cell culture of the invention is performed in a stirred culture vessel-system and a microcarrier-based process type is employed. In the microcarrier-based process the cells have migrated into the internal structure of the carriers (macroporous carriers) or have attached themselves to the surface of the carriers (solid carriers), or both. In a microcarrier-based process the eukaryote cells, the microcarriers and the culture medium are supplied to a culture vessel initially. In the following days additional culture medium may be fed if the culture volume was not brought to the final working volume of the vessel from the start. During the following period periodic harvest of product-containing culture supernatant and replacement with new medium is performed, until the culture is finally terminated. When harvesting product-containing supernatant the agitation, e.g., stirring, of the culture is stopped and the cell-containing carriers are allowed to sediment following which part of the product-containing culture medium is removed.

Propagation steps: Before reaching the production phase where regular harvesting of product-containing culture supernatant for further down-stream processing is performed, the cells are propagated according to any scheme or routine that may be suitable for the particular cell in question. The propagation phase may be a single step or a multiple step procedure. In a single step propagation procedure the cells are removed from storage and inoculated directly to the culture vessel containing the microcarriers where the production is going to take place. In a multiple step propagation procedure the cells are removed from storage and propagated through a number of culture vessels of gradually increasing size until reaching the final culture vessel containing microcarriers where production is going to take place. During the propagation steps the cells are grown under conditions that are optimized for growth. Culture conditions, such as temperature, pH, dissolved oxygen and the like, are those known to be optimal for the particular cell and will be apparent to the skilled person or artisan within this field (see, e.g., *Animal Cell Culture: A Practical Approach* 2$^{nd}$ *Ed.*, Rickwood, D. and Hames, B. D., eds., Oxford University Press, New York (1992)).

In one embodiment of the present invention the cell culture process is operated in one culture vessel: The cells are inoculated directly into the culture vessel containing microcarriers where the production is going to take place; the cells are propagated until a suitable cell density is reached and the production phase is initiated.

In another embodiment of the present invention the cell culture process is operated in at least two distinct culture vessels: One or more seed culture vessel(s) (first propagation step(s)) followed by the production culture vessel (last propagation step followed by production phase). In the first propagation step the cells expressing the desired polypeptide are inoculated into a seed culture vessel containing culture medium and propagated until the cells reach a minimum cross-seeding density. Subsequently, the propagated seed culture is transferred to the production culture vessel containing (a) culture medium and (b) microcarriers. In this culture vessel the cells are cultured under conditions in which the cells migrate onto the surface of the solid carriers or the exterior and interior surfaces of the macroporous carriers, and they continue to grow in this last propagation step until the carriers are fully colonised by the cells. During this last propagation step medium exchange is performed by allowing the microcarriers to settle to the bottom of the culture vessel, after which a predetermined percentage of the tank volume is removed and a corresponding percentage tank volume of fresh medium is added to the vessel. The microcarriers are then re-suspended in the medium and this process of medium removal and replacement are repeated at a predetermined interval, for example every 24 hours. The amount of replaced medium depends on the cell density and may typically be from 10-95%, preferably from 25% to 80%, of the tank volume as shown in Table 1 below.

It will be understood that in a process where the propagation phase is a multiple step procedure the propagation may take place in culture vessels of progressively increasing size until a sufficient number of cells is obtained for entering the final culture vessel. For example, one or more seed culture vessels of 5 l, 50 l, 100 l or 500 l may be used sequentially. A seed culture vessel typically has a capacity of between 5 l and 1000 l. Typically, cells are inoculated into a seed culture vessel at an initial density of about 0.2 to 0.4×10$^6$ cells/ml and propagated until the culture reaches a cell density of about 1.0×10$^6$ cells/ml. Typically, a minimum cross-seeding density is between 0.8 and about 1.5×10$^6$ cells/ml.

Some of the setpoints that are suitable for the production of a desired polypeptide, e.g., factor VII, are not necessarily suitable for the initial growth of the cells, either in seed culture or on the microcarriers. For example, temperature, DOT, and/or pH may be different for the two phases. The medium exchanges during propagation is done to keep the cells alive and growing, not to harvest culture supernatant for down-stream processing.

Possible culture conditions for the last propagation step in the final culture vessel (containing microcarriers) are outlined in Table 1, below.

TABLE 1

| Setpoint | Range | Preferred range | More preferred Value |
|---|---|---|---|
| PH | 6-8 | 6.6-7.6 | 7.0 |
| Temperature | 28-40° C. | 34-38° C. | 36-37° C. |
| Dissolved Oxygen Tension | 10-90% of saturation | 20-80% of saturation | 50% of saturation |
| Daily Medium | | | |

TABLE 1-continued

| Setpoint | Range | Preferred range | More preferred Value |
|---|---|---|---|
| Change: | | | |
| % of medium changed at | 10-35% of medium exchanged at 0.4-1.0 × $10^6$ cells ml−1 | 25% of medium exchanged at 0.4-1.0 × $10^6$ cells ml−1 | 25% of medium exchanged at 0.5 × $10^6$ cells ml−1 |
| % of medium changed at | 30-70% of medium exchanged at 0.7-3.0 × $10^6$ cells ml−1 | 50% of medium exchanged at 0.7-3.0 × $10^6$ cells ml−1 | 50% of medium exchanged at 1.0 × $10^6$ cells ml−1 |
| % of medium changed at | 60-90% of medium exchanged at 1.0-12.0 × $10^6$ cells ml−1 | 80% of medium exchanged at 1.0-12.0 × $10^6$ cells ml−1 | 80% of medium exchanged at 2.0-10 × $10^6$ cells ml−1 |

Production Phase: When the cell density reaches the value suitable for start of production phase, i.e. for having product-containing culture supernatant down-stream processed, 60-95% of the culture supernatant is harvested every 24 hours, preferably 80%. This value of cell density is typically 1-12×$10^6$ cells per ml. Setpoints may be changed at this point and set at values suitable for production of the desired polypeptide.

The medium exchange is performed by allowing the microcarriers to settle to the bottom of the tank, after which the selected percentage of the tank volume is removed and a corresponding percentage tank volume of fresh medium is added to the vessel. Between 25 and 90% of the tank volume are typically replaced; preferably, 80% of the tank volume is replaced with fresh medium. The microcarriers are then re-suspended in the medium and this process of medium removal and replacement are typically repeated every 10 to 48 hours; preferably, every 24 hours.

An outline of this aspect of the process is shown in Table 2.

TABLE 2

| Setpoint | Range | Preferred range | More preferred Value |
|---|---|---|---|
| PH | 6-8 | 6.6-7.6 | 7.0 for CHO and 6.7-6.9 for BHK |
| Temperature | 26-40° C. | 30-37° C. | 36° C. |
| Dissolved Oxygen Tension | 10-90% of saturation | 20-80% of saturation | 50% |
| % of medium changed | 25-90% of medium exchanged every 10-48 hours | 80% of medium changed every 10-48 hours | 80% of medium changed every 24 hours |

Optionally, a drop in temperature set point of the cultivation may be employed when entering, and during, the production phase.

When entering the production phase temperature, operating pH and medium exchange frequency are typically changed to values that are optimal for production. Examples of temperature ranges and values in growth and production phase, respectively, can be seen from Tables 1 and 2. A temperature of about 36° C. is preferred for a CHO cell line during the production phase.

Microcarriers: As used herein, microcarriers are particles which are small enough to allow them to be used in suspension cultures (with a stirring rate that does not cause significant shear damage to cells). They are solid, porous, or have a solid core with a porous coating on the surface. Microcarriers may, for example, without limitation, be cellulose- or dextran-based, and their surfaces (exterior and interior surface in case of porous carriers) may be positively charged.

In one series of embodiments, the microcarriers have an overall particle diameter between about 150 and 350 um; and have a positive charge density of between about 0.8 and 2.0 meq/g. In one series of embodiments, the microcarrier is a solid carrier. Useful solid microcarriers include, without limitation, Cytodex 1™ and Cytodex 2™ (Amersham Pharmacia Biotech, Piscataway N.J.). Solid carriers are particularly suitable for adhesion cells (anchorage-dependent cells).

In another series of embodiments, the microcarrier is a macroporous carrier. As used herein, macroporous carriers are particles, e.g. cellulose-based, which have the following properties: (a) They are small enough to allow them to be used in suspension cultures (with a stirring rate that does not cause significant shear damage to cells); and (b) they have pores and interior spaces of sufficient size to allow cells to migrate into the interior spaces of the particle. Their surfaces (exterior and interior) may in one embodiment be positively charged. In one series of embodiments, the carriers: (a) have an overall particle diameter between about 150 and 350 um; (b) have pores having an average pore opening diameter of between about 15 and about 40 um; and (c) have a positive charge density of between about 0.8 and 2.0 meq/g. In some embodiments, the positive charge is provided by DEAE (N,N,-diethylaminoethyl) groups. Useful macroporous carriers include, without limitation, Cytopore 1™ and Cytopore 2™ (Amersham Pharmacia Biotech, Piscataway N.J.). Particularly preferred are Cytopore 1™ carriers, which have a mean particle diameter of 230 um, an average pore size of 30 um, and a positive charge density of 1.1 meq/g.

Large-scale culture conditions: As used herein, a large-scale culture vessel has a capacity of at least about 100 l, preferably at least about 500 l, more preferably at least about 1000 l and most preferably at least about 5000 l. In case that the cell culture process is operated in at least two distinct culture vessels, such as one or more seed culture vessel(s) (first propagation step(s)) followed by the production culture vessel (last propagation step followed by production phase), then the process typically involves transferring about 50 l of the propagated seed culture (having about 1.0×$10^6$ cells/ml) into a 500 l culture vessel containing 150 l of culture medium.

The large-scale culture is maintained under appropriate conditions of, e.g., temperature, pH, dissolved oxygen tension (DOT), and agitation rate, and the volume is gradually increased by adding medium to the culture vessel. In case of a microcarrier process the culture vessel also comprises an amount of microcarriers corresponding to a final microcarrier concentration in the range of 1 to 10 g/l. After the transfer, the cells typically migrate onto the surface of the carriers or into the interior of the carriers within the first 24 hours. The term "large-scale process" may be used interchangeably with the term "industrial-scale process". Furthermore, the term "culture vessel" may be used interchangeably with "tank", "reactor", "fermentor" and "bioreactor".

Cells: In practising the present invention, the cells being cultivated are preferably eukaryote cells, more preferably an established eukaryote cell line, including, without limitation, CHO (e.g., ATCC CCL 61), COS-1 (e.g., ATCC CRL 1650), baby hamster kidney (BHK), and HEK293 (e.g., ATCC CRL 1573; Graham et al., *J. Gen. Virol.* 36:59-72, 1977) cell lines. A preferred BHK cell line is the tk⁻ ts13 BHK cell line (Waechter and Baserga, *Proc. Natl. Acad. Sci. USA* 79:1106-1110, 1982), hereinafter referred to as BHK 570 cells. The BHK 570 cell line is available from the American Type Culture Collection, 12301 Parklawn Dr., Rockville, Md. 20852, under ATCC accession number CRL 10314. A tk⁻ ts13 BHK cell line is also available from the ATCC under accession number CRL 1632.

A preferred CHO cell line is the CHO K1 cell line available from ATCC under accession number CC161.

Other suitable cell lines include, without limitation, Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1); DUKX cells (CHO cell line) (Urlaub and Chasin, *Proc. Natl. Acad. Sci. USA* 77:4216-4220, 1980) (DUKX cells also being referred to as DXB11 cells), and DG44 (CHO cell line) (*Cell*, 33: 405, 1983, and *Somatic Cell and Molecular Genetics* 12: 555, 1986). Also useful are 3T3 cells, Namalwa cells, myelomas and fusions of myelomas with other cells. In some embodiments, the cells may be mutant or recombinant cells, such as, e.g., cells that express a qualitatively or quantitatively different spectrum of enzymes that catalyze post-translational modification of proteins (e.g., glycosylation enzymes such as glycosyl transferases and/or glycosidases, or processing enzymes such as propeptides) than the cell type from which they were derived. Suitable insect cell lines also include, without limitation, *Lepidopteral* cell lines, such as *Spodoptera frugiperda* cells or *Trichoplusia ni* cells (see, e.g., U.S. Pat. No. 5,077,214).

In some embodiments, the cells used in practising the invention are capable of growing in suspension cultures. As used herein, suspension-competent cells are those that can grow in suspension without making large, firm aggregates, i.e., cells that are monodisperse or grow in loose aggregates with only a few cells per aggregate. Suspension-competent cells include, without limitation, cells that grow in suspension without adaptation or manipulation (such as, e.g., hematopoietic cells or lymphoid cells) and cells that have been made suspension-competent by gradual adaptation of attachment-dependent cells (such as, e.g., epithelial or fibroblast cells) to suspension growth.

The cells used in practising the invention may be adhesion cells (also known as anchorage-dependent or attachment-dependent cells). As used herein, adhesion cells are those that need to adhere or anchor themselves to a suitable surface for propagation and growth. In one embodiment of the invention, the cells used are adhesion cells. In these embodiments, both the propagation phases and the production phase include the use of microcarriers. The used adhesion cells should be able to migrate onto the carriers (and into the interior structure of the carriers if a macroporous carrier is used) during the propagation phase(s) and to migrate to new carriers when being transferred to the production bioreactor. If the adhesion cells are not sufficiently able to migrate to new carriers by themselves, they may be liberated from the carriers by contacting the cell-containing microcarriers with proteolytic enzymes or EDTA. The medium used (particularly when free of animal-derived components) should furthermore contain components suitable for supporting adhesion cells; suitable media for cultivation of adhesion cells are available from commercial suppliers, such as, e.g., Sigma.

The cells may also be suspension-adapted or suspension-competent cells. If such cells are used, the propagation of cells may be done in suspension, thus microcarriers are only used in the final propagation phase in the production culture vessel itself and in the production phase. In case of suspension-adapted cells the microcarriers used are typically macroporous carriers wherein the cells are attached by means of physical entrapment inside the internal structure of the carriers.

Medium: The terms "cell culture medium" and "culture medium" refer to a nutrient solution used for growing eukaryote cells that typically provides at least one component from one or more of the following categories: (1) salts of e.g. sodium, potassium, magnesium, and calcium contributing to the osmolality of the medium; (2) an energy source, usually in the form of a carbohydrate such as glucose; (3) all essential amino acids, and usually the basic set of twenty amino acids; (4) vitamins and/or other organic compounds required at low concentrations; and (5) trace elements, where trace elements are defined as inorganic compounds that are typically required at very low concentrations, usually in the micromolar range. The nutrient solution may optionally be supplemented with one or more of the components from any of the following catagories: (a) animal serum; (b) hormones and other growth factors such as, for example, insulin, transferrin, and epidermal growth factor; and (c) hydrolysates of protein and tissues.

The present invention encompasses cultivating eukaryote cells in medium comprising animal-derived components, e.g. serum or serum components, as well as medium lacking animal-derived components. The cell culture medium comprising animal-derived components (such as, e.g., fetal bovine serum (FBS)) may comprise more than 5% serum or between 0-5% serum, such as, for example, between 0-1% serum or 0-0.1% serum. Medium lacking animal-derived components are preferred. As used herein, "animal-derived" components are any components that are produced in an intact animal (such as, e.g., proteins isolated and purified from serum), or produced by using components produced in an intact animal (such as, e.g., an amino acid made by using an enzyme isolated and purified from an animal to hydrolyse a plant source material). By contrast, a protein which has the sequence of an animal protein (i.e., has a genomic origin in an animal) but which is produced in vitro in cell culture (such as, e.g., in a recombinant yeast or bacterial cell or in an established continuous eukaryote cell line, recombinant or not), in media lacking components that are produced in, and isolated and purified from an intact animal is not an "animal-derived" component (such as, e.g., insulin produced in a yeast or a bacterial cell, or insulin produced in an established mammal cell line, such as, e.g., CHO, BHK or HEK cells, or interferon produced in Namalwa cells). For example, a protein which has the sequence of an animal protein (i.e., has a genomic origin in an animal) but which is produced in a recombinant cell in media lacking animal derived components (such as, e.g., insulin produced in a yeast or bacterial cell) is not an "animal-derived component". Accordingly, a cell culture medium lacking animal-derived components is one that may contain animal proteins that are recombinantly produced; such medium, however, does not contain, e.g., animal serum or proteins or other products purified from animal serum. Such medium may, for example, contain one or more components derived from plants. Any cell culture medium, in particular one lacking animal-derived components, that supports cell growth and maintenance under the conditions of the invention may be used. Typically, the medium contains water, an osmolality regulator, a buffer, an energy source, amino acids, an inorganic or recombinant iron source, one or more synthetic or recombinant growth factors, vitamins, and cofactors. In one embodiment, the medium lacks animal-derived components and lacks proteins ("protein-free"). Media lacking animal-derived components and/or proteins are available from commercial suppliers, such as, for example, Sigma, JRH Biosciences, Gibco and Gemini.

In addition to conventional components, a medium suitable for producing factor VII or factor VII-related polypeptides contains Vitamin K, which is required for γ-carboxylation of glutamic acid residues in factor VII, at a concentration between about 0.1-50 mg/liter, preferably between about 0.5-25 mg/liter, more preferably between about 1-10 mg/liter and most preferably about 5 mg/liter.

Suitable media for use in the present invention are available from commercial suppliers such as, for example, Gibco, and JRH Biosciences.

In one embodiment, the medium is composed as shown in Table 3, optionally supplemented with one or more of the components shown in Table 4.

The table below (Table 3) is a composition of a medium suitable for use in the present invention. Optionally, one or more of the components listed in Table 4 is/are added to the culture medium. Preferred ranges are listed in Table 4. In one embodiment, the medium used is Medium 318-X; in another embodiment, it is medium CHO-K.

TABLE 3

| COMPONENT | Range (mg/l) | Concentration in CHO—K (mg/l) | Concentration in 318-X (mg/l) |
|---|---|---|---|
| Sodium chloride | 0-70000 | 6122 | 6996 |
| Potassium chloride | 0-3118 | 311.8 | 311.8 |
| Sodium Dihydrogen Phosphate monohydrate | 0-625 | 62.5 | 62.5 |
| Sodium hydrogen carbonate | 0-27 | — | 2.7 |
| Disodium hydrogen phosphate anhydrous | 0-710 | 71.02 | — |
| Disodium hydrogen phosphate 7 hydrate | 0-1340 | — | 134 |
| Magnesium chloride anhydrous | 0-287 | 28.64 | — |
| Magnesium chloride 6 hydrate | 0-610 | — | 61 |
| Magnesium sulphate anhydrous | 0-488 | 48.84 | — |
| Magnesium sulphate 7 hydrate | 0-1000 | — | 100 |
| Calcium chloride anhydrous | 0-1166 | 116.6 | 116.6 |
| Copper sulphate 5 hydrate | 0-0.014 | 0.0013 | 0.0013 |
| Ferrous sulphate 7 hydrate | 0-4.17 | 0.147 | 0.417 |
| Ferric nitrate 9 hydrate | 0-0.5 | 0.05 | 0.05 |
| Ferric citrate | 0-123 | 0.4 | 12.24 |
| Zinc sulphate 7 hydrate | 0-0.44 | 0.432 | 0.432 |
| Dextrose anhydrous | 0-45000 | 4501 | 4500 |
| Linoleic acid | 0-12 | 1.189 | 0.336 |
| Insulin | 0-50 | 5 | 5 |
| DL 68 Thioctic Acid | 0-9 | 0.473 | 0.84 |

TABLE 3-continued

| COMPONENT | Range (mg/l) | Concentration in CHO—K (mg/l) | Concentration in 318-X (mg/l) |
|---|---|---|---|
| l-alanine | 0-50 | 4.45 | 4.45 |
| l-arginine chloride | 0-5500 | 547.8 | 447.5 |
| l-asparagine monohydrate | 0-6010 | 407.5 | 607.5 |
| l-aspartic acid | 0-1100 | 6.65 | 106.65 |
| l-cysteine hydrochloride monohydrate | 0-1200 | 117.65 | 77.56 |
| l-glutamic acid | 0-2500 | 251.35 | 107.35 |
| Glycine | 0-190 | 18.75 | 18.75 |
| l-histidine hydrochloride monohydrate | 0-2200 | 211.48 | 101.48 |
| l-isoleucine | 0-750 | 54.47 | 74.47 |
| l-leucine | 0-1800 | 179.05 | 159.05 |
| l-lysine hydrochloride | 0-2400 | 231.25 | 131.25 |
| l-methionine | 0-1380 | 137.24 | 97.24 |
| l-phenylalanine | 0-1600 | 155.48 | 85.48 |
| l-proline | 0-1150 | 17.25 | 117.25 |
| l-serine | 0-4300 | 266.25 | 426.25 |
| l-threonine | 0-1800 | 173.45 | 73.45 |
| l-tryptophan | 0-2100 | 39.02 | 209.02 |
| l-tyrosine disodium dihydrate | 0-900 | 55.79 | 85.79 |
| l-valine | 0-1800 | 177.85 | 125.85 |
| l-cystine dihydrochloride | 0-320 | 31.29 | 31.29 |
| Sodium hypoxanthine | 0-25 | 2.39 | 2.39 |
| Putrescine dihydrochloride | 0-1 | 0.081 | 0.081 |
| Sodium pyruvate | 0-2300 | 220 | 55 |
| D-Biotin | 0-3 | 0.1313 | 0.259 |
| D-calcium pantothenate | 0-60 | 4.08 | 6 |
| Folic acid | 0-70 | 4.65 | 6.65 |
| I-inositol | 0-700 | 39.1 | 65.6 |
| Nicotinamide | 0-50 | 3.085 | 4.2 |
| Choline chloride | 0-450 | 29.32 | 42 |
| Pyridoxine hydrochloride | 0-25 | 0.117 | 2.2 |
| Riboflavin | 0-3 | 0.219 | 0.219 |
| Thiamine hydrochloride | 0-35 | 2.67 | 3.17 |
| Thymidine | 0-4 | 0.365 | 0.365 |
| Vitamin B12 | 0-50 | 2.68 | 4.68 |
| Pyridoxal hydrochloride | 0-60 | 6 | 2 |
| Glutathione | 0-50 | 2.5 | 5 |
| Sodium Selenite | 0-0.5 | 0.02175 | 0.0232 |
| l-ascorbic acid | 0-50 | 27.5 | 5 |
| Pluronic F68 | 0-10000 | 1000 | 1000 |
| Vitamin K | 0-50 | 5 | 5 |
| Dextran T 70 | 0-1000 | — | 100 |
| HY-SOY | 0-5000 | 500 | — |

Optional Components:

TABLE 4

| Component | Range (mg/l) |
|---|---|
| Vegetable hydrolysates HyPep 4601, 4602, 4605, 5603, 7401 | 0-5000 |
| Lipids Oleic acid | 0-15 |
| Growth Factors HGR, IGF, EGF | 0-50 |

In another embodiment, the medium used has the following composition (318-U medium):

TABLE 5

| COMPONENT | MG/L |
|---|---|
| Sodium Chloride | 6122 |
| Potassium Chloride | 311.8 |

TABLE 5-continued

| COMPONENT | |
|---|---|
| Sodium Dihydrogen Phosphate Monohydrate | 62.5 |
| Disodium Hydrogen Phosphate Anhydrous | 71.02 |
| Magnesium Chloride Anhydrous | 28.64 |
| Magnesium Sulphate Anhydrous | 48.84 |
| Calcium Chloride Anhydrous | 116.6 |
| Copper Sulphate 5-hydrate | 0.0013 |
| Ferrous Sulphate 7-hydrate | 0.417 |
| Ferric Nitrate 9-hydrate | 0.05 |
| Zinc Sulphate 7-hydrate | 0.432 |
| Dextrose Anhydrous | 4501 |
| Linoleic Acid | 1.189 |
| DL-68-Thioctic Acid | 0.473 |
| L-Alanine | 4.45 |
| L-Arginine Hydrochloride | 547.5 |
| L-Asparagine Monohydrate | 407.5 |
| L-Aspartic Acid | 6.65 |
| L-Cysteine Hydrochloride Monohydrate | 117.65 |
| L-Glutamic Acid | 251.35 |
| L-Glutamine | 365 |
| Glycine | 18.75 |
| L-Histidine Hydrochloride Monohydrate | 211.48 |
| L-Isoleucine | 54.47 |
| L-Leucine | 179.05 |
| L-Lysine Hydrochloride | 231.25 |
| L-Methionine | 137.24 |
| L-Phenylalanine | 155.48 |
| L-Proline | 17.25 |
| L-Serine | 266.25 |
| L-Threonine | 173.45 |
| L-Tryptophan | 39.02 |
| L-Tyrosine Disodium Dihydrate | 55.79 |
| L-Valine | 177.85 |
| L-Cystine Dihydrochloride | 31.29 |
| Sodium Hypoxanthine | 2.39 |
| Putrescine Dihydrochloride | 0.081 |
| Sodium Pyruvate | 220 |
| D-Biotin | 0.1313 |
| D-Calcium Pantothenate | 4.08 |
| Folic Acid | 4.65 |
| I-Inositol | 39.1 |
| Nicotinamide | 3.085 |
| Choline Chloride | 29.32 |
| Pyridoxine Hydrochloride | 0.117 |
| Riboflavin | 0.219 |
| Thiamine Hydrochloride | 2.67 |
| Thymidine | 0.365 |
| Vitamin B12 | 2.68 |
| Pyridoxal Hydrochloride | 3 |
| Glutathione | 2.5 |
| Sodium Selenite | 0.02175 |
| L-Ascorbic Acid, Free Acid | 27.5 |
| Sodium Hydrogen Carbonate | 2440 |
| HySoy (soy protein hydrolysate) | 500 |
| Ethanolamin | 1.22 |
| Insulin | 5 |
| Dextran T70 | 100 |
| Pluronic F68 | 1000 |
| Vitamin K1 | 5 |
| | ML/L |
| Fe/citrat complex (50 mM/1 M) | 0.4 |
| Mercaptoethanol | 0.0035 |

The medium is preferably a medium lacking animal-derived components, or a medium lacking animal-derived components and lacking proteins ("protein-free").

In one embodiment the medium is a commercially available protein-free CHO medium lacking animal-derived components (JRH Biosciences) and the cell line is a CHO cell. In one embodiment, the medium is 318-X Medium and the cell line is a BHK cell line; in another embodiment, the medium is 318-U Medium and the cell line is a BHK cell line. In another embodiment, the medium is CHO-K Medium and the cell line is a CHO cell line.

In some embodiments, the cells used in practising the present invention are adapted to suspension growth in medium lacking animal-derived components, such as, e.g., medium lacking serum. Such adaptation procedures are described, e.g., in Scharfenberg, et al., *Animal Cell Technology Developments towards the 21st Century*, E. C. Beuvery et al. (Eds.), Kluwer Academic Publishers, pp. 619-623, 1995 (BHK and CHO cells); Cruz, *Biotechnol. Tech.* 11:117-120, 1997 (insect cells); Keen, *Cytotechnol.* 17:203-211, 1995 (myeloma cells); Berg et al., *Biotechniques* 14:972-978, 1993 (human kidney 293 cells). In a particularly preferred embodiment, the host cells are BHK 21 or CHO cells that have been engineered to express human Factor VII and that have been adapted to grow in the absence of serum or animal-derived components.

Culture vessels: The culture vessels may be e.g. conventional stirred tank reactors (CSTR) where agitation is obtained by means of conventional impeller types or airlift reactors where agitation is obtained by means of introducing air from the bottom of the vessel. Among the parameters controlled within specified limits are pH, dissolved oxygen tension (DOT), and temperature. The pH may be controlled by e.g. varying the carbon dioxide ($CO_2$) concentration in the headspace gas and by addition of base to the culture liquid when required. Dissolved oxygen tension may be maintained by e.g. sparging with air or pure oxygen or mixtures thereof. The temperature-control medium is water, heated or cooled as necessary. The water may be passed through a jacket surrounding the vessel or through a piping coil immersed in the culture.

Processing steps: Once the medium has been removed from the culture vessel, it may be subjected to one or more processing steps to obtain the desired protein, including, without limitation, centrifugation or filtration to remove cells that were not immobilized in the carriers; affinity chromatography, hydrophobic interaction chromatography; ion-exchange chromatography; size exclusion chromatography; electrophoretic procedures (e.g., preparative isoelectric focusing (IEF), differential solubility (e.g., ammonium sulfate precipitation), or extraction and the like. See, generally, Scopes, *Protein Purification*, Springer-Verlag, New York, 1982; and *Protein Purification*, J.-C. Janson and Lars Ryden, editors, VCH Publishers, New York, 1989.

Purification of Factor VII or Factor VII-related polypeptides may involve, e.g., affinity chromatography on an anti-Factor VII antibody column (see, e.g., Wakabayashi et al., *J. Biol. Chem.* 261:11097, 1986; and Thim et al., *Biochem.* 27:7785, 1988) and activation by proteolytic cleavage, using Factor XIIa or other proteases having trypsin-like specificity, such as, e.g., Factor IXa, kallikrein, Factor Xa, and thrombin. See, e.g., Osterud et al., *Biochem.* 11:2853 (1972); Thomas, U.S. Pat. No. 4,456,591; and Hedner et al., *J. Clin. Invest.* 71:1836 (1983). Alternatively, Factor VII may be activated by passing it through an ion-exchange chromatography column, such as Mono Q® (Pharmacia) or the like.

Polypeptides for Large-Scale Production: In some embodiments, the cells used in practising the invention are human cells expressing an endogenous Factor VII gene. In these cells, the endogenous gene may be intact or may have been modified in situ, or a sequence outside the Factor VII gene may have been modified in situ to alter the expression of the endogenous Factor VII gene.

In other embodiments, cells from any eukaryote source are engineered to express human Factor VII from a recombinant gene. As used herein, "Factor VII" or "Factor VII polypeptide" encompasses wild-type Factor VII (i.e., a polypeptide having the amino acid sequence disclosed in U.S. Pat. No. 4,784,950), as well as variants of Factor VII exhibiting substantially the same or improved biological activity relative to wild-type Factor VII. The term "Factor VII" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa.

As used herein, "Factor VII-related polypeptides" encompasses polypeptides, including variants, in which the Factor VIIa biological activity has been substantially modified or reduced relative to the activity of wild-type Factor VIIa. These polypeptides include, without limitation, Factor VII or Factor VIIa into which specific amino acid sequence alterations have been introduced that modify or disrupt the bioactivity of the polypeptide.

The biological activity of Factor VIIa in blood clotting derives from its ability to (i) bind to tissue factor (TF) and (ii) catalyze the proteolytic cleavage of Factor IX or Factor X to produce activated Factor IX or X (Factor IXa or Xa, respectively). For purposes of the invention, Factor VIIa biological activity may be quantified by measuring the ability of a preparation to promote blood clotting using Factor VII-deficient plasma and thromboplastin, as described, e.g., in U.S. Pat. No. 5,997,864. In this assay, biological activity is expressed as the reduction in clotting time relative to a control sample and is converted to "Factor VII units" by comparison with a pooled human serum standard containing 1 unit/ml Factor VII activity. Alternatively, Factor VIIa biological activity may be quantified by (i) measuring the ability of Factor VIIa to produce of Factor Xa in a system comprising TF embedded in a lipid membrane and Factor X. (Persson et al., J. Biol. Chem. 272:19919-19924, 1997); (ii) measuring Factor X hydrolysis in an aqueous system; (iii) measuring its physical binding to TF using an instrument based on surface plasmon resonance (Persson, FEBS Letts. 413:359-363, 1997) and (iv) measuring hydrolysis of a synthetic substrate.

Factor VII variants having substantially the same or improved biological activity relative to wild-type Factor VIIa encompass those that exhibit at least about 25%, preferably at least about 50%, more preferably at least about 75% and most preferably at least about 90% of the specific activity of Factor VIIa that has been produced in the same cell type, when tested in one or more of a clotting assay, proteolysis assay, or TF binding assay as described above. Factor VII variants having substantially reduced biological activity relative to wild-type Factor VIIa are those that exhibit less than about 25%, preferably less than about 10%, more preferably less than about 5% and most preferably less than about 1% of the specific activity of wild-type Factor VIIa that has been produced in the same cell type when tested in one or more of a clotting assay, proteolysis assay, or TF binding assay as described above. Factor VII variants having a substantially modified biological activity relative to wild-type Factor VII include, without limitation, Factor VII variants that exhibit TF-independent Factor X proteolytic activity and those that bind TF but do not cleave Factor X.

Variants of Factor VII, whether exhibiting substantially the same or better bioactivity than wild-type Factor VII, or, alternatively, exhibiting substantially modified or reduced bioactivity relative to wild-type Factor VII, include, without limitation, polypeptides having an amino acid sequence that differs from the sequence of wild-type Factor VII by insertion, deletion, or substitution of one or more amino acids.

Non-limiting examples of Factor VII variants having substantially the same biological activity as wild-type Factor VII include S52A-FVIIa, S60A-FVIIa (Lino et al., Arch. Biochem. Biophys. 352: 182-192, 1998); FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Kornfelt et al., Arch. Biochem. Biophys. 363:43-54, 1999); FVII variants as disclosed in PCT/DK02/00189; and FVII variants exhibiting increased proteolytic stability as disclosed in WO 02/38162 (Scripps Research Institute); FVII variants having a modified Gla-domain and exhibiting an enhanced membrane binding as disclosed in WO 99/20767 (University of Minnesota); and FVII variants as disclosed in WO 01/58935 (Maxygen ApS).

Non-limiting examples of FVII variants having increased biological activity compared to wild-type FVIIa include FVII variants as disclosed in WO 01/83725, WO 02/22776; WO 02/38162 (Scripps Research Institute); NN ansøgninger; and FVIIa variants with enhanced activity as disclosed in JP 2001061479 (Chemo-Sero-Therapeutic Res Inst.).

Non-limiting examples of Factor VII variants having substantially reduced or modified biological activity relative to wild-type Factor VII include R152E-FVIIa (Wildgoose et al., Biochem 29:3413-3420, 1990), S344A-FVIIa (Kazama et al., J. Biol. Chem. 270:66-72, 1995), FFR-FVIIa (Holst et al., Eur. J. Vasc. Endovasc. Surg. 15:515-520, 1998), and Factor VIIa lacking the Gla domain, (Nicolaisen et al., FEBS Letts. 317:245-249, 1993).

Examples of factor VII or factor VII-related polypeptides include, without limitation, wild-type Factor VII, L305V-FVII, L305V/M306D/D309S-FVII, L3051-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, S336G-FVII; S52A-Factor VII, S60A-Factor VII; R152E-Factor VII, S344A-Factor VII, Factor VIIa lacking the Gla domain; and P11Q/K33E-FVII, T106N-FVII, K143N/N145T-FVII, V253N-FVII, R290N/A292T-FVII, G291N-FVII, R315N/V317T-FVII, K143N/N145T/R315N/V317T-FVII; and FVII having substitutions, additions or deletions in the amino acid sequence from 233Thr to 240Asn, FVII having substitutions, additions or deletions in the amino acid sequence from 304Arg to 329Cys.

The present invention also encompasses cultivation, preferably large-scale cultivation, of eukaryote cells that express one or more proteins of interest, whether from endogenous genes or subsequent to introduction into such cells of recombinant genes encoding the protein. Such proteins include, without limitation, Factor VIII; Factor IX; Factor X; Protein C; tissue factor; rennin; growth hormone, including human growth hormone; bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β platelet-derived growth factor (PDGF); fibroblast growth factor such as α-FGF and β-FGF; epidermal growth factor (EGF); transforming growth factor (TGF) such as TGF-alpha and TGF-beta, insulin-like growth factor-I and -II (IGF-I and IGF-II); CD proteins such as CD-3, CD-4, CD-8, and CD-19; erythropoietin; osteoinductive factors; immunotoxins; bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressin; regulatory proteins; antibodies; and fragments of any of the above polypeptides.

The following examples are intended as non-limiting illustrations of the present invention.

EXAMPLES

Example 1

Preparation of CHO Cell

A plasmid vector pLN174 for expression of human FVII has been described (Persson and Nielsen. 1996. FEBS Lett. 385: 241-243). Briefly, it carries the cDNA nucleotide sequence encoding human FVII including the propeptide under the control of a mouse metallothionein promoter for transcription of the inserted cDNA, and mouse dihydrofolate reductase cDNA under the control of an SV40 early promoter for use as a selectable marker.

For construction of a plasmid vector encoding a gamma-carboxylation recognition sequence, a cloning vector pBluescript II KS+ (Stratagene) containing cDNA encoding FVII including its propeptide was used (pLN171). (Persson et al. 1997. J. Biol. Chem. 272: 19919-19924). A nucleotide sequence encoding a stop codon was inserted into the cDNA encoding FVII after the propeptide of FVII by inverse PCR-mediated mutagenesis on this cloning vector. The template plasmid was denatured by treatment with NaOH followed by PCR with Pwo (Boehringer-Mannheim) and Taq (Perkin-Elmer) polymerases with the following primers:

(SEQ ID NO. 1)
5'-AGC GTT TTA GCG CCG GCG CCG GTG CAG GAC-3'

(SEQ ID NO. 2)
5'-CGC CGG CGC TAA AAC GCT TTC CTG GAG GAG CTG CGG CC-3'

The resulting mix was digested with DpnI to digest residual template DNA and *Escherichia coli* were transformed with the PCR product. Clones were screened for the presence of the mutation by sequencing. The cDNA from a correct clone was transferred as a BamHI-EcoRI fragment to the expression plasmid pcDNA3 (Invitrogen). The resulting plasmid was termed pLN329. CHO K1 cells (ATCC CC161) were transfected with equal amounts of pLN174 and pLN329 with the Fugene6 method (Boehriner-Mannheim). Transfectants were selected by the addition of methotrexate to 1 μM and G-418 to 0.45 mg/ml. The pool of transfectants were cloned by limiting dilution and FVII expression from the clones was measured.

A high producing clone was further subcloned and a clone E11 with a specific FVII expression of 2.4 pg/cell/day in Dulbecco-modified Eagle's medium with 10% fetal calf serum was selected. The clone was adapted to serum free suspension culture in a commercially available CHO medium (JRH Bioscience) free of animal derived components.

Example 2

Production of Factor VII

Summary of Experimental Conditions

The commercially available protein-free medium for CHO cells free of animal-derived components (JRH Biosciences) was supplemented with insulin (5 mg/L) and vitamin K1 (5 mg/L) throughout all three cultivations in the example.

The size of the culture vessel was 500 l. The process type was standard Cytopore 1 microcarrier culture with daily batch wise exchange of 80% of the medium (400 L) after sedimentation of carriers.

In cultivations FFF 1239 and FFF 1242 a cooling step was applied each day immediately before the sedimentation of carriers at medium exchange (cooling to 26° C. in FFF 1239; cooling to 26° C. up to day 19 followed by cooling to 20° C. up to day 53 in FFF 1242).

Throughout all three cultivations standard set points were used for the cultivation parameters temperature, pH, and dissolved oxygen. The temperature set point was 36.0° C. The pH set points were 7.10 for regulation downwards (by addition of $CO_2$-gas to headspace) and 6.80 for regulation upwards (by addition of sodium carbonate solution to the culture liquid). The set point for dissolved oxygen was 50% of saturation with air.

Summary of Results and Conclusions

In the first of the three cultivations, FFF 1235, the high producing CHO clone (as described in Example 1) was cultured in a standard microcarrier process and no cooling step was applied. As can be seen from FIG. 1 the graph over FVII titres versus time was "bell-shaped", i.e., a decline in FVII titres was seen, in this cultivation from day 18-20 onwards. It was obvious that the decline was caused by a decline in the total cell density in the culture vessel, i.e. by a loss of cells from the culture vessel.

During the cooling steps performed before sedimentation of carriers in FFF 1239 and FFF 1242 the valve for cooling water to the jacket was kept constantly open. The temperature of the cooling water, which was the only parameter decisive for the duration of the cooling step, was 10-15° C. Cooling down from 36.0° C. to 26.0° C. and 20.0° C., respectively, took around 30 minutes and 55 minutes, respectively. The new medium added to the culture vessel after harvesting of old medium was pre-heated to 30° C. After addition of new medium, the temperature control loop of the culture vessel was activated with set point 36.0° C., and the subsequent heating to the set point took around 120 minutes, irrespective of the target temperature before sedimentation of carriers (26.0° C. or 20.0° C.).

The overall profile of the two cultivations, FFF 1239 and FFF 1242, where daily cooling steps were applied, were similar to cultivation FFF 1235. The daily cooling steps applied immediately before sedimentation of carriers in FFF 1239 and FFF 1242 did have a positive effect on the cell densities and the FVII titres. Although the graphs were still "bell-shaped" the cooling steps did increase the peak values of cell densities and FVII titres (peak FVII titre in FFF 1239 36 mg/L versus 22 mg/L in FFF 1235) as well as extend the period with high cell densities and high FVII titres (period with FVII titres above 15 mg/L extended from 8-9 days in FFF 1235 to 13-14 days in FFF 1239). It can be seen that cooling to 26° C. resulted in the highest cell densities and FVII titres.

Results

Graphical Presentations

FVII titres in FFF 1235, FFF 1239, and FFF 1242 are shown graphically in FIG. 1.

Cell counts and FVII titres for cultivations FFF 1235, FFF 1239, and FFF 1242 are shown in FIG. 2 to FIG. 4.

The overall conclusion drawn from cultivations FFF 1239 and FFF 1242 is that a cooling step before the daily sedimentation of carriers does have a positive effect on the overall performance of the culture, and that 26° C. is to be preferred to 20° C.

All patents, patent applications, and literature references referred to herein are hereby incorporated by reference in their entirety.

Many variations of the present invention will suggest themselves to those skilled in the art in light of the above detailed description. Such obvious variations are within the full intended scope of the appended claims.

(ii) actively cooling the culture to a predetermined temperature prior to step (iii), wherein the predetermined temperature is −10° C. below the setpoint;

(iii) sedimenting the microcarriers; and (iv) harvesting all or part of the culture medium thereby producing said Factor VII polypeptide thereby producing said Factor VII polypeptide.

2. The method according to claim 1, further comprising a step of adding fresh medium to the culture after said harvesting.

3. The method according to claim 1, further comprising a step of recovering said polypeptide from the harvested culture medium.

4. The method according to claim 1, wherein the culture is cooled to a temperature from 25° C. to 27° C.

5. The method according to claim 1, wherein the eukaryote cells are insect cells.

6. The method according to claim 1, wherein the eukaryote cells are mammalian cells.

7. The method according to claim 6, wherein the mammalian cells are selected from the group consisting of human embryonic kidney (HEK), baby hamster kidney (BHK), and Chinese hamster ovary (CHO) cells.

8. The method according to claim 7, wherein the mammalian cells are CHO cells.

9. The method according to claim 1, wherein the Factor VII polypeptide is produced at a level at least 15 mg/l of culture.

The invention claimed is:

1. A method for production of a Factor VII polypeptide in eukaryote cells, comprising the steps of (i) culturing cells expressing a Factor VII polypeptide on microcarriers under conditions and at a setpoint temperature appropriate for expression of said Factor VII polypeptide;

10. The method according to claim 1, wherein the Factor VII polypeptide is human Factor VII, the cells are CHO cells, the microcarriers are macroporous carriers, the set-point temperature is 36° C., and the culture is cooled to 26° C. before allowing the microcarriers to sediment.

* * * * *

UNITED STATES PATENT AND TRADEMARK OFFICE
CERTIFICATE OF CORRECTION

| | | |
|---|---|---|
| PATENT NO. | : 7,947,471 B2 | Page 1 of 1 |
| APPLICATION NO. | : 11/851549 | |
| DATED | : May 24, 2011 | |
| INVENTOR(S) | : Ida Molgaard Knudsen | |

It is certified that error appears in the above-identified patent and that said Letters Patent is hereby corrected as shown below:

Column 20, Claim 1, Line 3: after "is" delete "-".

Signed and Sealed this
Ninth Day of August, 2011

David J. Kappos
*Director of the United States Patent and Trademark Office*